United States Patent
Shameli et al.

(10) Patent No.: US 11,786,296 B2
(45) Date of Patent: Oct. 17, 2023

(54) INSTRUMENT FOR ENDOSCOPIC POSTERIOR NASAL NERVE ABLATION

(71) Applicant: ACCLARENT, INC., Irvine, CA (US)

(72) Inventors: Ehsan Shameli, Irvine, CA (US); Babak Ebrahimi, Irvine, CA (US); Fatemeh Akbarian, Rancho Palos Verdes, CA (US); William J. Kane, Newport Coast, CA (US); Athanasios Papadakis, Newport Beach, CA (US)

(73) Assignee: Accularent, Inc., Irvine, CA (US)

( * ) Notice: Subject to any disclaimer, the term of this patent is extended or adjusted under 35 U.S.C. 154(b) by 114 days.

(21) Appl. No.: 16/783,626

(22) Filed: Feb. 6, 2020

(65) Prior Publication Data
US 2020/0261149 A1 Aug. 20, 2020

Related U.S. Application Data

(60) Provisional application No. 62/806,009, filed on Feb. 15, 2019.

(51) Int. Cl.
*A61B 18/14* (2006.01)
*A61B 18/00* (2006.01)
*A61B 1/00* (2006.01)

(52) U.S. Cl.
CPC .... *A61B 18/1485* (2013.01); *A61B 1/000094* (2022.02); *A61B 2018/00327* (2013.01);
(Continued)

(58) Field of Classification Search
CPC ...... A61B 18/1485; A61B 2018/00577; A61B 2018/00434; A61B 2018/00791;
(Continued)

(56) References Cited

U.S. PATENT DOCUMENTS

| 5,078,716 A | 1/1992 | Doll |
| 5,733,282 A | 3/1998 | Ellman et al. |

(Continued)

FOREIGN PATENT DOCUMENTS

| CN | 1222843 A | 7/1999 |
| CN | 1224338 A | 7/1999 |

(Continued)

OTHER PUBLICATIONS

Heathline, Esophagus, 2018 (Year: 2018).*

(Continued)

*Primary Examiner* — Linda C Dvorak
*Assistant Examiner* — Mystee Nguyen Delgado
(74) *Attorney, Agent, or Firm* — Frost Brown Todd LLP

(57) ABSTRACT

A surgical instrument includes an elongate shaft having a proximal shaft portion and a malleable distal shaft portion. The elongate shaft is configured to be secured to a supporting surgical instrument. An ablation head is coupled to the malleable distal shaft portion and includes at least one electrode operable to deliver RF energy to tissue for ablating the tissue. The ablation head is sized to fit within the nasal cavity of a patient with a distal end of the supporting surgical instrument. The proximal shaft portion is configured to operatively couple with an RF energy source operable to energize the at least one electrode with RF energy. The malleable distal shaft portion is configured to bend relative to a longitudinal shaft axis defined by the proximal shaft portion for selectively orienting the ablation head relative to the longitudinal shaft axis.

20 Claims, 6 Drawing Sheets

(52) U.S. Cl.
CPC ............... *A61B 2018/00434* (2013.01); *A61B 2018/00577* (2013.01); *A61B 2018/00791* (2013.01); *A61B 2018/00982* (2013.01)

(58) Field of Classification Search
CPC .......... A61B 2018/00982; A61B 2018/00327; A61B 2018/00702; A61B 2018/0016; A61B 2018/00178; A61B 2018/0091; A61B 1/05; A61B 17/24; A61B 2018/00202; A61B 2018/00875; A61B 1/00009; A61B 1/00016; A61B 1/0051; A61B 1/273; A61B 1/00087; A61B 1/0014; A61B 2017/00296
USPC .......................... 606/41; 600/104, 105, 101
See application file for complete search history.

(56) References Cited

U.S. PATENT DOCUMENTS

| | | | |
|---|---|---|---|
| 5,792,135 | A | 8/1998 | Madhani et al. |
| 6,045,549 | A | 4/2000 | Smethers, II |
| 6,109,268 | A | 8/2000 | Thapliyal et al. |
| 6,139,545 | A | 10/2000 | Utley et al. |
| 6,210,355 | B1 | 4/2001 | Edwards et al. |
| 6,361,531 | B1 | 3/2002 | Hissong |
| 6,416,512 | B1 | 7/2002 | Ellman et al. |
| 6,447,510 | B1 | 9/2002 | Ellman et al. |
| 6,526,318 | B1 | 2/2003 | Ansarinia |
| 6,562,036 | B1 | 5/2003 | Ellman et al. |
| 6,572,613 | B1 | 6/2003 | Ellman et al. |
| 6,911,027 | B1 | 6/2005 | Edwards et al. |
| 6,920,883 | B2 | 7/2005 | Bessette et al. |
| 7,001,380 | B2 | 2/2006 | Goble |
| 7,004,941 | B2 | 2/2006 | Tvinnereim et al. |
| 7,297,143 | B2 | 11/2007 | Woloszko et al. |
| 7,377,918 | B2 | 5/2008 | Amoah |
| 7,491,200 | B2 | 2/2009 | Underwood |
| 7,720,521 | B2 | 5/2010 | Chang et al. |
| 7,842,034 | B2 | 11/2010 | Mittelstein et al. |
| 7,862,560 | B2 | 1/2011 | Marion |
| 7,892,230 | B2 | 2/2011 | Woloszko |
| 8,290,582 | B2 | 10/2012 | Lin et al. |
| 8,298,243 | B2 | 10/2012 | Carlton et al. |
| 8,479,969 | B2 | 7/2013 | Shelton, IV |
| 8,512,335 | B2 | 8/2013 | Cheng et al. |
| 8,573,465 | B2 | 11/2013 | Shelton, IV |
| 8,747,401 | B2 | 6/2014 | Gonzalez et al. |
| 8,783,541 | B2 | 7/2014 | Shelton, IV et al. |
| 8,800,838 | B2 | 8/2014 | Shelton, IV |
| 8,900,227 | B2 | 12/2014 | Stierman |
| 8,936,594 | B2 | 1/2015 | Wolf et al. |
| 8,961,510 | B2 | 2/2015 | Alshemari |
| 8,979,842 | B2 | 3/2015 | McNall, III et al. |
| 9,011,428 | B2 | 4/2015 | Nguyen et al. |
| 9,072,597 | B2 | 7/2015 | Wolf et al. |
| 9,393,067 | B2 | 7/2016 | van der Burg |
| 9,415,194 | B2 | 8/2016 | Wolf et al. |
| 9,474,915 | B2 | 10/2016 | Gonzales et al. |
| 9,532,796 | B2 | 1/2017 | DuBois et al. |
| 9,649,144 | B2 | 5/2017 | Aluru et al. |
| 9,687,288 | B2 | 6/2017 | Saadat |
| 10,028,781 | B2 | 7/2018 | Saadat |
| 11,602,260 | B2* | 3/2023 | Saadat ..................... A61B 1/05 |
| 2003/0208250 | A1 | 11/2003 | Edwards et al. |
| 2004/0204747 | A1 | 10/2004 | Kemeny et al. |
| 2005/0283148 | A1 | 12/2005 | Janssen et al. |
| 2006/0004323 | A1 | 1/2006 | Chang et al. |
| 2006/0052776 | A1 | 3/2006 | Desinger et al. |
| 2006/0178670 | A1 | 8/2006 | Woloszko et al. |
| 2007/0027451 | A1 | 2/2007 | Desinger et al. |
| 2007/0073282 | A1 | 3/2007 | McGaffigan et al. |
| 2007/0118104 | A1* | 5/2007 | Wallace ............. A61B 18/1492 606/41 |
| 2008/0027423 | A1 | 1/2008 | Choi et al. |
| 2008/0027505 | A1 | 1/2008 | Levin et al. |
| 2009/0012513 | A1* | 1/2009 | Utley ................. A61B 18/1492 606/191 |
| 2010/0030031 | A1* | 2/2010 | Goldfarb ............ A61B 1/00183 600/173 |
| 2010/0274164 | A1 | 10/2010 | Juto |
| 2011/0160740 | A1 | 6/2011 | Makower et al. |
| 2011/0288412 | A1* | 11/2011 | Deckman ............. A61B 8/0833 600/439 |
| 2012/0029498 | A1 | 2/2012 | Branovan |
| 2012/0101494 | A1 | 4/2012 | Cadouri et al. |
| 2012/0316557 | A1 | 12/2012 | Sartor et al. |
| 2014/0100557 | A1 | 4/2014 | Bohner et al. |
| 2014/0324037 | A1 | 10/2014 | Hoey et al. |
| 2014/0364725 | A1 | 12/2014 | Makower |
| 2015/0150624 | A1 | 6/2015 | Petersohn |
| 2016/0058495 | A1 | 3/2016 | Twomey |
| 2016/0058500 | A1 | 3/2016 | Sharp et al. |
| 2016/0256181 | A1 | 9/2016 | Allen, IV et al. |
| 2016/0331459 | A1 | 11/2016 | Townley et al. |
| 2017/0165459 | A1 | 6/2017 | Gross et al. |
| 2017/0197075 | A1 | 7/2017 | Van Bruggen et al. |
| 2017/0231474 | A1* | 8/2017 | Saadat ............... A61B 1/00105 600/107 |
| 2018/0078327 | A1 | 3/2018 | Lin et al. |
| 2018/0103994 | A1 | 4/2018 | Fox et al. |
| 2018/0116711 | A1 | 5/2018 | Suh |
| 2018/0133460 | A1 | 5/2018 | Townley et al. |
| 2018/0177541 | A1 | 6/2018 | Regadas |
| 2018/0177546 | A1 | 6/2018 | Dinger et al. |
| 2018/0193052 | A1 | 7/2018 | Govari et al. |
| 2018/0228533 | A1 | 8/2018 | Wolf et al. |
| 2018/0263678 | A1 | 9/2018 | Saadat |
| 2019/0374280 | A1 | 12/2019 | Salazar et al. |
| 2020/0000516 | A1* | 1/2020 | Branovan .......... A61B 18/1477 |

FOREIGN PATENT DOCUMENTS

| | | |
|---|---|---|
| EP | 1049413 A1 | 11/2000 |
| EP | 1189543 A1 | 3/2002 |
| EP | 1416870 A4 | 5/2004 |
| EP | 3027133 A4 | 6/2016 |
| EP | 3030183 A1 | 6/2016 |
| EP | 3157454 B1 | 4/2017 |
| EP | 3258864 A1 | 12/2017 |
| GB | 2545559 A | 6/2017 |
| WO | WO 1999/003411 A1 | 1/1999 |
| WO | WO 1999/020185 A1 | 4/1999 |
| WO | WO 1999/030655 A1 | 6/1999 |
| WO | WO 2001/012089 A1 | 2/2001 |
| WO | WO 2008/079476 A2 | 7/2008 |
| WO | WO 2011/005903 A2 | 1/2011 |
| WO | WO 2011/025830 A1 | 3/2011 |
| WO | WO 2018/075273 A1 | 4/2018 |

OTHER PUBLICATIONS

E Papesch, The nasal pyriform aperture and its importance, 2016 (Year: 2016).*

Healthline, Esophagus, (Year: 2018).*

International Search Report and Written Opinion dated May 18, 2020 for International Application No. PCT/IB2020/051091, 19 pages.

Fukutake, Tomoshige, et al. "Laser surgery for allergic rhinitis." *Archives of Otolaryngology—Head & Neck Surgery* 112.12 (1986): 1280-1282.

Gindros, George, et al. "Mucosal changes in chronic hypertrophic rhinitis after surgical turbinate reduction." *European archives of oto-rhino-laryngology* 266.9 (2009): 1409-1416.

Ho, Ki-Hong Kevin, et al. "Electromechanical reshaping of septal cartilage." *The Laryngoscope* 113.11 (2003): 1916-1921.

* cited by examiner ental factors. Conventional treatments for rhinitis include antihistamines, topical or systemic corticosteroids, and topical anticholinergics, for example.
INSTRUMENT FOR ENDOSCOPIC POSTERIOR NASAL NERVE ABLATION

PRIORITY

This application claims the benefit of U.S. Provisional Pat. App. No. 62/806,009, entitled "Instrument for Endoscopic Posterior Nasal Nerve Ablation," filed Feb. 15, 2019, the disclosure of which is incorporated by reference herein.

BACKGROUND

Rhinitis is a medical condition that presents as irritation and inflammation of the mucous membrane within the nasal cavity. The inflammation results in the generation of excessive amounts of mucus, which can cause runny nose, nasal congestion, sneezing, and/or post-nasal drip. Allergenic rhinitis is an allergic reaction to environmental factors such as airborne allergens, while non-allergenic (or "vasomotor") rhinitis is a chronic condition that presents independently of environmental factors. Conventional treatments for rhinitis include antihistamines, topical or systemic corticosteroids, and topical anticholinergics, for example.

For cases of intractable rhinitis in which the symptoms are severe and persistent, an additional treatment option is the surgical removal of a portion of the vidian (or "pterygoid") nerve—a procedure known as vidian neurectomy. The theoretical basis for vidian neurectomy is that rhinitis is caused by an imbalance between parasympathetic and sympathetic innervation of the nasal cavity, and the resultant over stimulation of mucous glands of the mucous membrane. Vidian neurectomy aims to disrupt this imbalance and reduce nasal mucus secretions via surgical treatment of the vidian nerve. However, in some instances, vidian neurectomy can cause collateral damage to the lacrimal gland, which is innervated by the vidian nerve. Such damage to the lacrimal gland may result in long-term health complications for the patient, such as chronic dry eye. Posterior nasal neurectomy, or surgical removal of a portion of the posterior nasal nerves, may be an effective alternative to vidian neurectomy for treating intractable rhinitis.

FIG. 1 depicts a left sagittal view of a portion of a patient's head, showing the nasal cavity (10), the frontal sinus (12), the sphenoid sinus (14), and the sphenoid bone (16). The nasal cavity (10) is bounded laterally by the nasal wall (18), which includes an inferior turbinate (20), a middle turbinate (22), and a superior turbinate (24). The vidian nerve (32) resides within the vidian (or "pterygoid") canal (30), which is defined in part by the sphenoid bone (16) and is located posterior to the sphenoid sinus (14), approximately in alignment with the middle turbinate (22). The vidian nerve (32) is formed at its posterior end by the junction of the greater petrosal nerve (34) and the deep petrosal nerve (36); and joins at its anterior end with the pterygopalatine ganglion (38), which is responsible for regulating blood flow to the nasal mucosa. The posterior nasal nerves (40) join with the pterygopalatine ganglion (38) and extend through the region surrounding the inferior turbinate (20).

While instruments and methods for performing vidian neurectomies and posterior nasal neurectomies are known, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
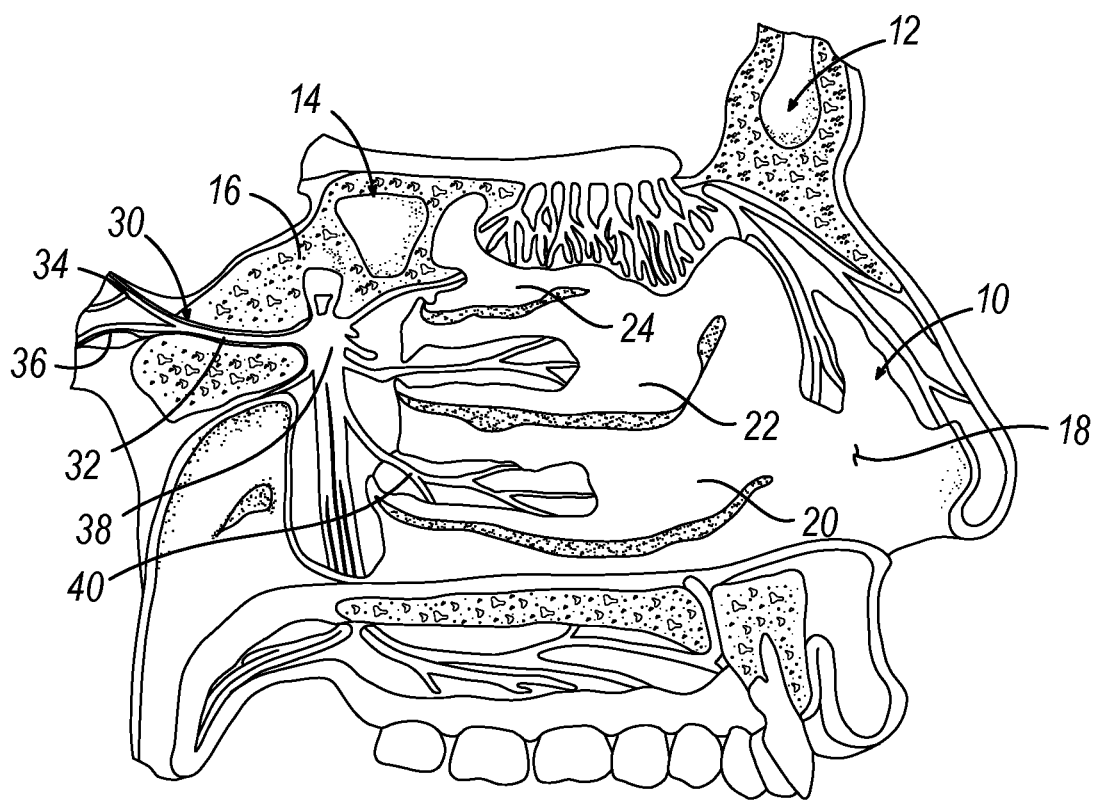
FIG. 1 depicts a left sagittal view of a portion of a patient's head, showing details of certain paranasal sinuses and nerves, including the vidian nerve and the posterior nasal nerve.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about," "approximately," and the like in connection with any numerical values or ranges of values are intended to encompass the exact value(s) referenced, as well as a suitable dimensional tolerance that enables the referenced feature or combination of features to function for the intended purpose described herein.

I. Overview of Exemplary RF Ablation Surgical System

Figure 2:
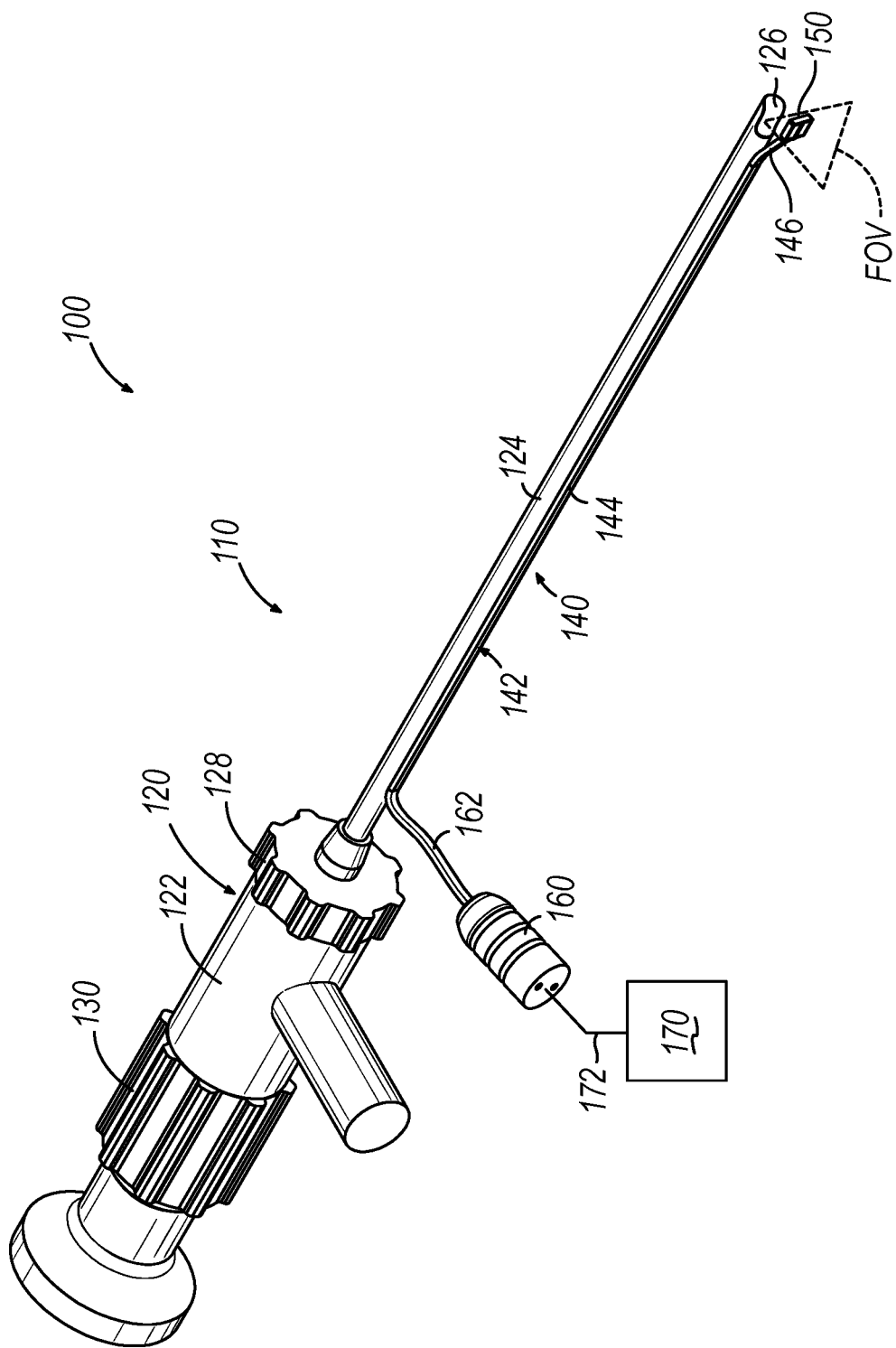
FIG. 2 depicts a schematic perspective view of an exemplary surgical system that includes a surgical instrument assembly defined by an endoscope and an RF ablation instrument in combination, and an RF energy source coupled with the RF ablation instrument.

FIG. 2 shows an exemplary RF ablation surgical system (100) operable to ablate a nerve, such as the posterior nasal neve (40), within the nasal cavity (10) of a patient with radio frequency (RF) energy. Surgical system (100) comprises a surgical instrument assembly (110) defined by a supporting surgical instrument in the form of an endoscope (120), and an RF ablation instrument (140) secured to an elongate rigid shaft (124) of endoscope (120). RF ablation instrument (140) is coupled with an RF generator (170) operable to deliver RF energy to an ablation head (150) of RF ablation instrument (140) for ablating tissue positioned in contact with ablation head (150), as described in greater detail below.

Figure 5:
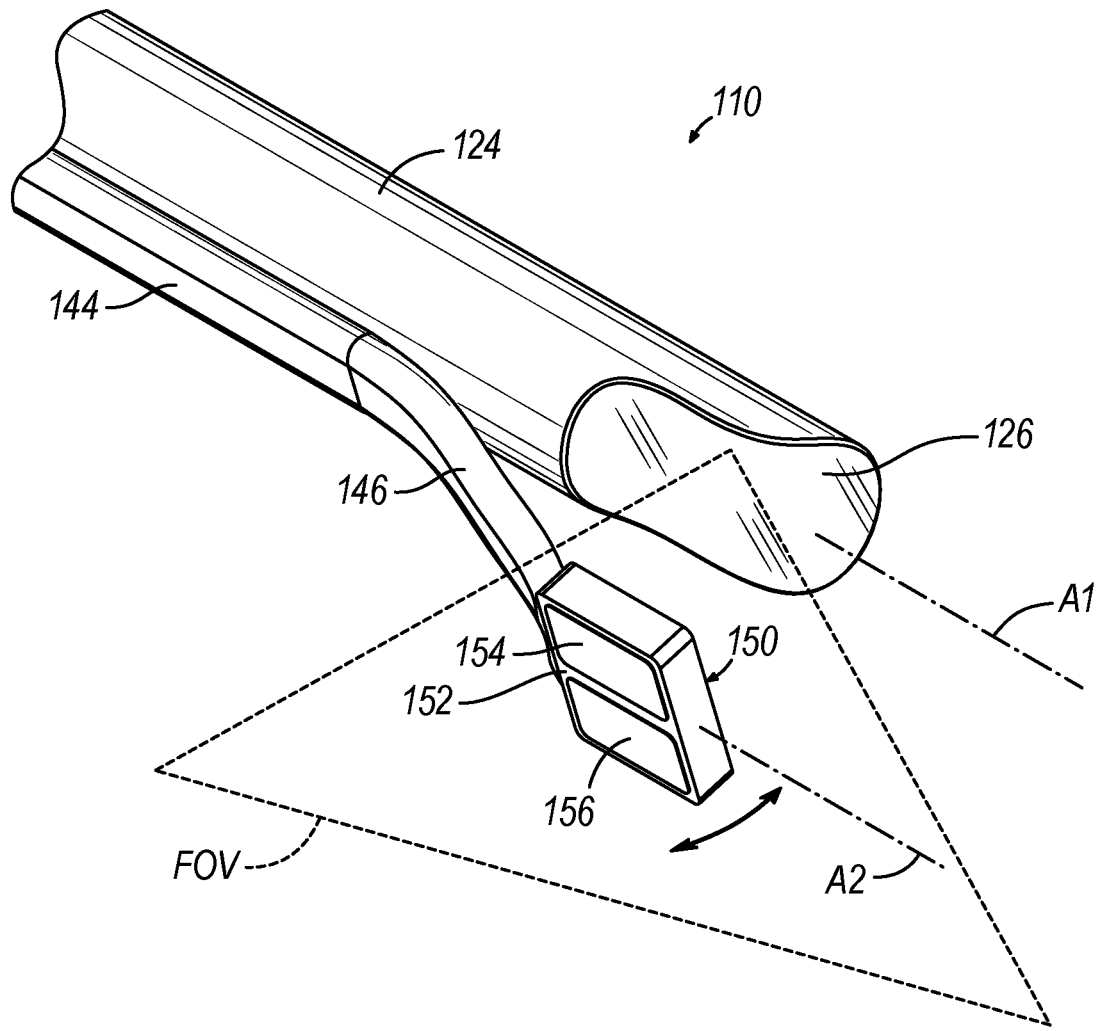
FIG. 5 depicts an enlarged perspective view of a distal portion of the surgical instrument assembly of FIG. 2.

Endoscope (120) of the present example includes a body (122) that may function as a handle, and an elongate rigid shaft (124) extending distally from body (122) along a central longitudinal axis (A1) (see FIG. 5). Endoscope shaft (124) is sized to be received within various anatomical passages of the human body, such as the ear, nose, and throat, for example. In one exemplary version, endoscope shaft (124) may have an outer diameter of approximately 4 mm and a working length of approximately 175 mm. A distal end of endoscope shaft (124) includes a window (126) through which an endoscopic image is captured in a field of view (FOV). Though not shown, the distal end of endoscope shaft (124) may house a moveable optical element in the form of a swing prism operable to provide endoscope (120) with a moveable field of view (FOV) through window (126), thereby enabling viewing along a variety of transverse viewing angles without having to flex endoscope shaft (124) within the anatomical passageway. Such a swing prism and related features of endoscope (120) may be configured in accordance with the teachings of U.S. Pat. Pub. No. 2010/0030031, entitled "Swing Prism Endoscope," published Feb. 4, 2010, now abandoned, the disclosure of which is incorporated by reference herein. Alternatively, endoscope (120) may take any other suitable form as will be apparent to those skilled in the art in view of the teachings herein.

To adjust the field of view (FOV) of endoscope (120), endoscope shaft (124) is selectively rotatable relative to body (122) about the central longitudinal axis (A1), and the swing prism (not shown) housed within the distal end of endoscope shaft (124) is selectively movable relative to endoscope shaft (124). To provide such adjustment, endoscope body (122) includes a distal dial (128) that is selectively rotatable about the central longitudinal axis (A1) of endoscope (120) to rotate endoscope shaft (124) relative to body (122) about the central longitudinal axis (A1). Body (122) further includes a proximal dial (130) that is selectively rotatable about the central longitudinal axis (A1) to pivot the swing prism (not shown) within and relative to endoscope shaft (124). Accordingly, selective actuation of dials (128, 130) enables an operator to move the field of view (FOV) of endoscope (120) to thereby visualize a particular anatomical region of interest within a patient during a procedure without having to flex endoscope shaft (124).

Figure 3:
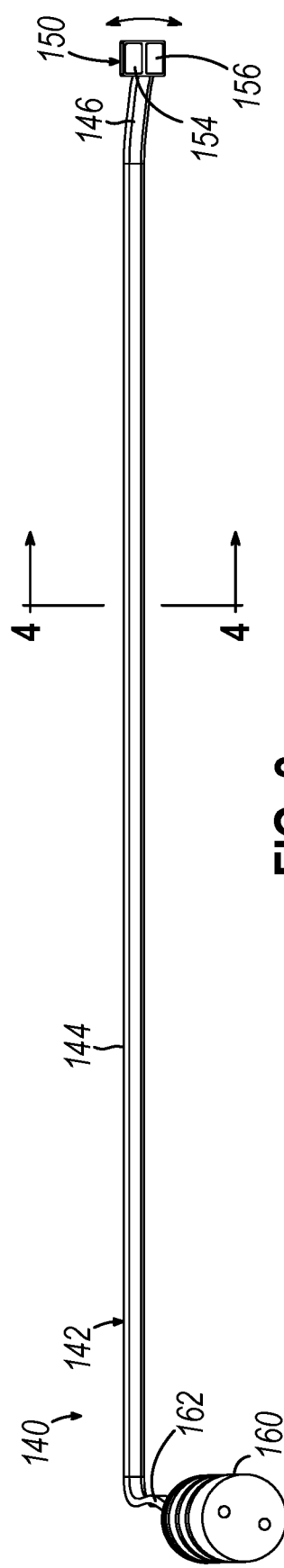
FIG. 3 depicts a perspective view of the RF ablation instrument of FIG. 2.

RF ablation instrument (140) is configured to be fixedly secured to and supported by rigid shaft (124) of endoscope (120) such that ablation head (150) is positioned with the field of view (FOV) of endoscope (120). Accordingly, an operator may visualize via endoscope (120) an ablation procedure being performed with RF ablation instrument (140), as described in greater detail below. As shown best in FIG. 3, RF ablation instrument (140) of the present example includes an elongate shaft (142) having a proximal shaft portion (144) and a distal shaft portion (146). At least distal shaft portion (146) is formed of a malleable material, such as nickel-titanium alloy (or "Nitinol"), such that distal shaft portion (146) is configured to bend relative to a longitudinal axis defined by proximal shaft portion (144). In some instances, an entirety of elongate shaft (142) may be formed of a malleable material such that shaft (142) may be bent to assume a variety of configurations as desired by an operator. As used herein in connection with elongate shaft (142) of RF ablation instrument (140), the terms "bend," "bent," and variations thereof mean plastic deformation in which the referenced portion of shaft (142) retains the shape to which it is formed by the operator.

As shown in FIG. 5, ablation head (150) extends distally from a distal end of distal shaft portion (146) of RF ablation instrument (140). Ablation head (150) of the present example is generally rectangular in shape but may be formed with a variety of other suitable shapes in other examples. A planar lower surface (152) of ablation head (150) supports a pair of electrodes (154, 156) positioned adjacent to one another. As described in greater detail below in connection with FIGS. 6-7B, electrodes (154, 156) are configured to cooperate to deliver bipolar RF energy to tissue (e.g., a nerve) positioned in contact with both electrodes (154, 156), to thereby ablate the tissue with RF energy. Electrodes (154, 156) of the present version are generally rectangular in shape and equal in size. In other versions, various other quantities, shapes, and arrangements of electrodes may be provided on ablation head (150) for ablating tissue with RF energy.

In some versions, ablation head (150) may include a single electrode configured to deliver monopolar RF energy to tissue positioned in contact with the electrode, in combination with a ground pad (not shown) positioned in contact with the patient's skin. Accordingly, it will be appreciated that ablation head (150) may be suitably configured to deliver bipolar or monopolar RF energy to tissue based on the selected surgical application. For instance, in surgical applications in which more localized treatment of tissue is desired, ablation head (150) may be configured with two or more electrodes (154, 156) operable to treat tissue with bipolar RF energy. For other surgical applications warranting a deeper treatment of the targeted tissue, ablation head (150) may be configured with a single RF electrode operable to treat tissue with monopolar RF energy. Furthermore, in addition to or in lieu of one or more RF ablation electrodes, ablation head (150) may include a resistance heating device, a cryoablation applicator, a chemical applicator, and/or an optical energy transmission device operable to ablate tissue.

In other examples, ablation head (150) may further comprise one or more tissue sensors operable to sense a condition of the tissue (e.g., a nerve) being ablated by electrodes (154, 156). Each such sensor may communicate a signal to a processor (not shown) of surgical system (100) indicating the sensed condition. In response to receiving the signal, the system processor may then regulate (e.g., deactivate) the RF ablation energy being delivered to electrodes (154, 156) from RF generator (170), and/or provide an indication to the operator informing of the sensed tissue condition. In some versions, ablation head (150) may include a tissue sensor in the form of a thermocouple (not shown) operable to measure a temperature of the tissue during ablation. In such versions, the system processor may deactivate delivery of RF ablation energy to electrodes upon determining that the sensed tissue temperature has reached a threshold temperature.

In other versions, ablation head (150) may include a tissue sensor in the form of a pair of detection electrodes operable to deliver a low power RF signal to the target tissue to measure an electrical impedance of the tissue during ablation. In some such versions, such detection electrodes may be provided separately from electrodes (154, 156) of ablatio head (150). In other such versions, electrodes (154, 156) may be operable as both ablation electrodes and as detection electrodes. In either configuration, the low power RF signal may be delivered to the target tissue simultaneously or in rapidly alternating fashion with the high-power RF ablation energy delivered by electrodes (154, 156). While the target tissue remains substantially intact and unablated, the low power RF signal will pass freely through the tissue with a relatively low impedance. As ablation of the tissue progresses, the detection electrodes will detect an increase in impedance of the tissue, which is communicated to the system processor.

As shown in FIG. 2, RF ablation instrument (140) further includes a proximal electrical connector (160) coupled with proximal shaft portion (144) by a cable (162). As shown schematically, proximal electrical connector (160) is configured to releasably couple with a separate cable (172), or another coupling device, that places RF ablation instrument (140) in electric communication with RF generator (170) so that RF generator (170) may deliver RF energy to electrodes (154, 156) of ablation head (150).

Figure 4:
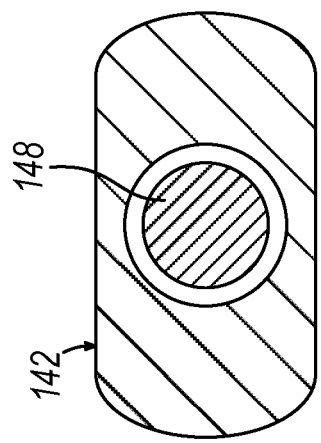
FIG. 4 depicts a cross-sectional view of the RF ablation instrument of FIG. 2, taken along section line 4-4 in FIG. 3.

As shown in FIG. 4, elongate shaft (142) of the present example houses an electrically conductive wire (148) that electrically couples electrodes (154, 156) of ablation head (150) with proximal electrical connector (160), such that RF energy may be transferred from RF generator (170) to electrodes (154, 156), via connector (160), cable (162), and wire (148). Though not shown, wire (148) and/or elongate shaft (142) itself may be shielded with a non-conductive material to prevent electrical shorting of RF ablation instrument (140) through elongate shaft (142), particularly in instances in which elongate shaft (142) itself is formed of an electrically conductive material. In some other versions of RF ablation instrument (140), wire (148) may be omitted and elongate shaft (142) (and optionally also ablation head (150)) may be formed of an electrically conductive material that electrically couples electrodes (154, 156) with proximal electrical connector (160). In such versions, elongate shaft (142) (and ablation head (150)) may be shielded with a non-conductive material to prevent electrical shorting of RF ablation instrument (140). Moreover, in such versions, electrodes (154, 156) may be defined by the same structure that defines ablation head (150).

As shown in FIGS. 2 and 5, and as discussed above, elongate shaft (142) of RF ablation instrument (140) is configured to be fixedly secured to rigid shaft of endoscope (120) such that ablation head (150) is positioned within the field of view (FOV) of endoscope (120). Such securement may be achieved with a variety of suitable methods that will be readily apparent to those of ordinary skill in the art. For instance, ablation instrument shaft (142) may be secured to endoscope shaft (124) with an adhesive or with heat shrink tubing, for example, thus providing the resulting instrument assembly (110) with a minimal outer diameter. Furthermore, ablation instrument shaft (142) may be secured to endoscope shaft (124) such that proximal shaft portion (144) of ablation instrument shaft (142) extends parallel to endoscope shaft (124).

As shown in FIG. 5, ablation head (150) extends distally from distal shaft portion (146) of RF ablation instrument (140) along a head axis (A2). The malleability of at least distal shaft portion (146) enables ablation head (150) to be selectively oriented by an operator such that head axis (A2) is offset from endoscope axis (A1), yet still parallel to endoscope axis (A1). In the configuration shown, ablation head (150) is oriented such that the electrode-supporting lower surface (152) of ablation head (150) faces away from endoscope window (126), and an opposed upper surface of ablation head (150) (not shown) faces toward endoscope window (126). As indicated by the directional arrows shown in FIGS. 3 and 5, distal shaft portion (146) may be bent by an operator to achieve any desired orientation of ablation head (150) relative to the proximal shaft portion (144) and the distal end of endoscope shaft (124). In this manner, ablation head (150) may be suitably positioned within the field of view (FOV) of endoscope (120) while maintaining a suitable lateral spacing from endoscope window (126) to enable effective RF ablation treatment while accommodating patient anatomy at the surgical site (e.g., within nasal cavity (10)).

Though not shown herein, RF ablation instrument (140) may be combined with features of an image-guided surgery (IGS) navigation system to further facilitate positioning of ablation head (150) within a patient. By way of example, such an IGS navigation system may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and/or U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

II. Exemplary Method of Ablating Posterior Nasal Nerve

Figure 6:
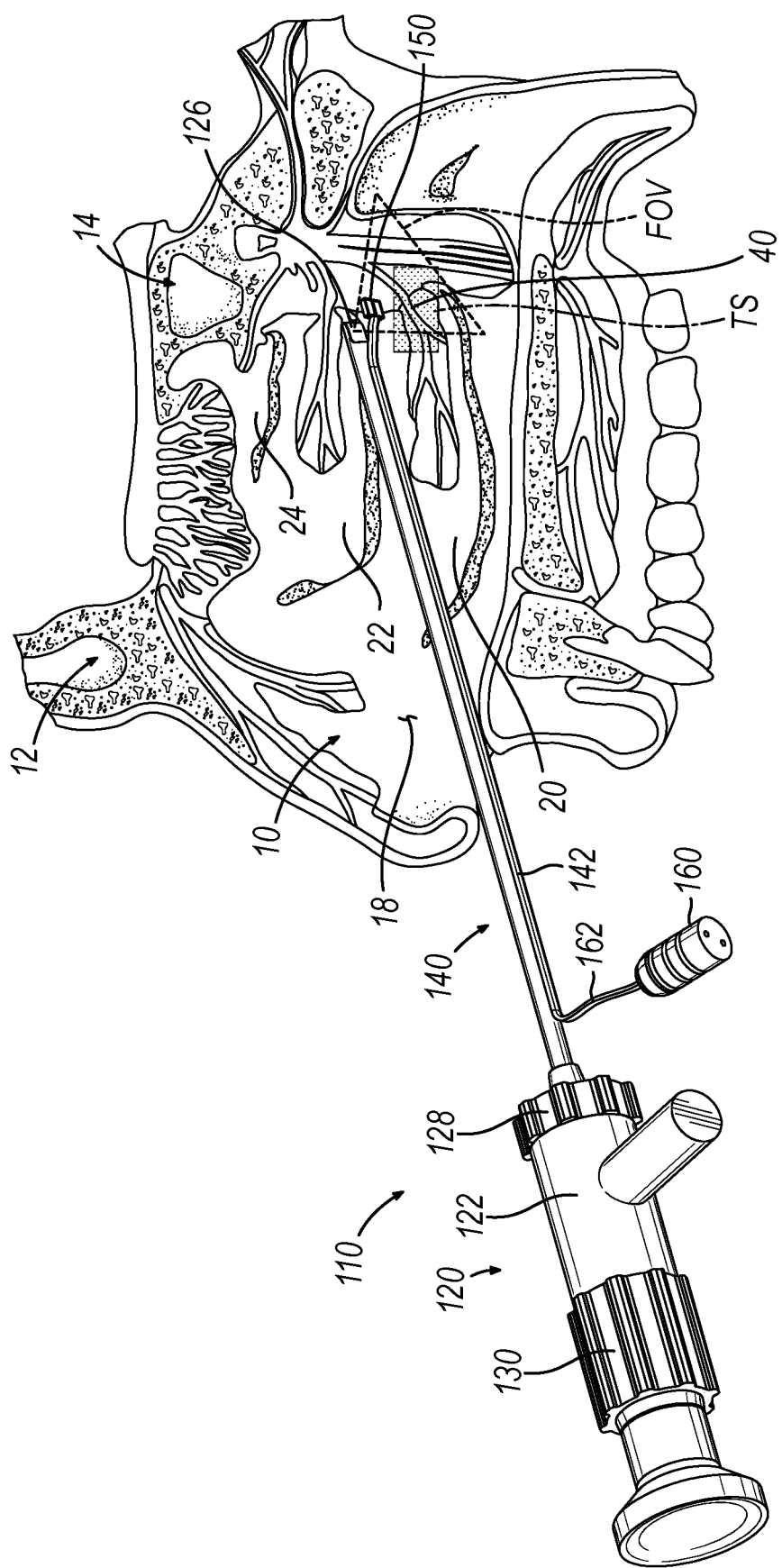
FIG. 6 depicts a right sagittal view of a portion of a patient's head with portions of a nasal wall shown broken away to reveal underlying nerves, showing an exemplary method for ablating a posterior nasal nerve of the patient at a treatment site within the nasal cavity with RF energy provided by the surgical system of FIG. 2.

Having described exemplary features of RF ablation surgical system (100) above, an exemplary method of performing a neurectomy on a posterior nasal nerve (40) of a patient with system (100) will now be described in connection with FIGS. 6-7B. While surgical system (100) is shown and described for treating a posterior nasal nerve, it will be appreciated that surgical system (100) may be employed in various other surgical applications for ablating other nerves within the nasal cavity (10), or for ablating tissues in various other anatomical regions of a patient. For instance, the teachings herein may be combined with at least some of the teachings of U.S. Pat. Pub. No. 2019/0374280, entitled "Apparatus and Method for Performing Vidian Neurectomy Procedure," published Dec. 12, 2019, issued as U.S. Pat. No. 11,625,805 on Apr. 11, 2023, the disclosure of which is incorporated by reference herein.

Before insertion of the distal end of instrument assembly (110) into the patient, distal shaft portion (146) of RF ablation instrument (140) is manually bent by the operator as needed to position ablation head (150) within the field of view (FOV) of endoscope (120). In the present example, distal shaft portion (146) (and optionally also a portion of proximal shaft portion (144)) is suitably bent such that ablation head (150) is offset from proximal shaft portion (144) and endoscope shaft (124), and such that electrodes (154, 156) face away from endoscope window (126), as described above in connection with FIG. 5.

The distal end of instrument assembly (110) is then inserted into the nasal cavity (10) of the patient and advanced toward a treatment site (TS) at the posterior ends of the inferior and middle turbinates (20, 22), under visualization provided by endoscope (120). While advancing toward the treatment site (TS), the operator manipulates endoscope (120) as needed to position electrodes (154, 156) of ablation head (150) in contact with the portion of nasal wall (18) in which the target posterior nasal nerve (40) resides. For instance, the operator may selectively rotate distal dial (128) of endoscope (120) to thereby rotate endoscope shaft (124) and thus RF ablation instrument (140) about the central endoscope axis (A1) to better position ablation head (150) relative to the posterior nasal nerve (40) at the treatment site (TS). Because ablation head (150) remains within the endoscope field of view (FOV) throughout this process, the operator is able to maintain visualization of ablation head (150) and thereby ensure accurate placement of ablation head (150) relative to the treatment site (TS). It will be appreciated that malleable distal shaft portion (146) of RF ablation instrument (140) may be provided with sufficient rigidity to resist unintended bending when ablation head (150) is pressed against nasal wall (18) with the minimum force necessary to maintain direct contact of electrodes (154, 156) with the nasal wall tissue to enable delivery of RF ablation energy.

Figure 7A:
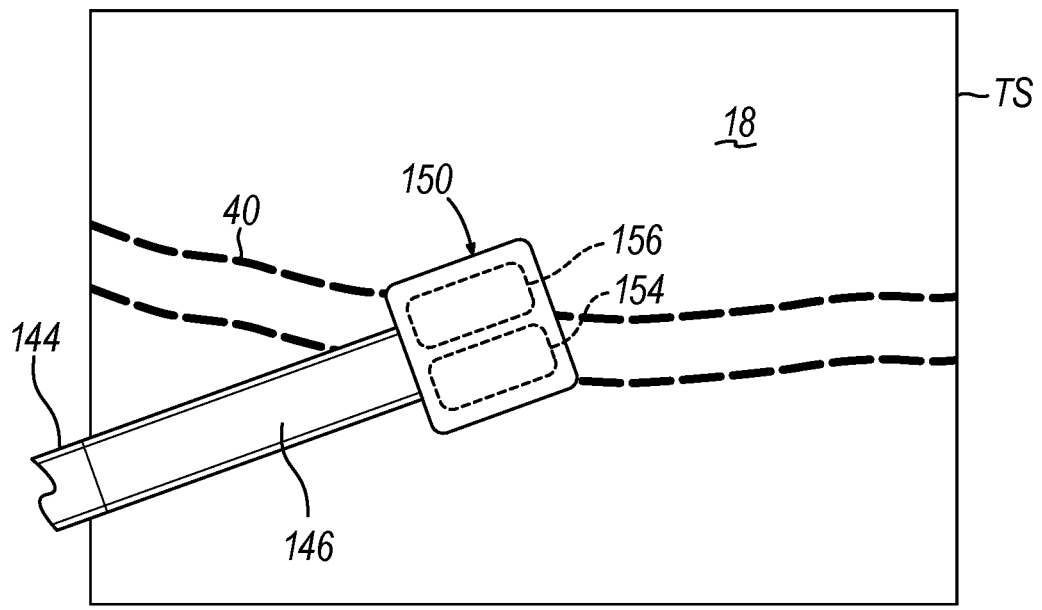
FIG. 7A depicts an enlarged schematic view of the treatment site of FIG. 6, showing an ablation head of the RF ablation instrument of FIG. 2 being applied to nasal wall tissue at the treatment site for ablating a posterior nasal nerve residing beneath the tissue in accordance with the method of FIG. 6.
Figure 7B:
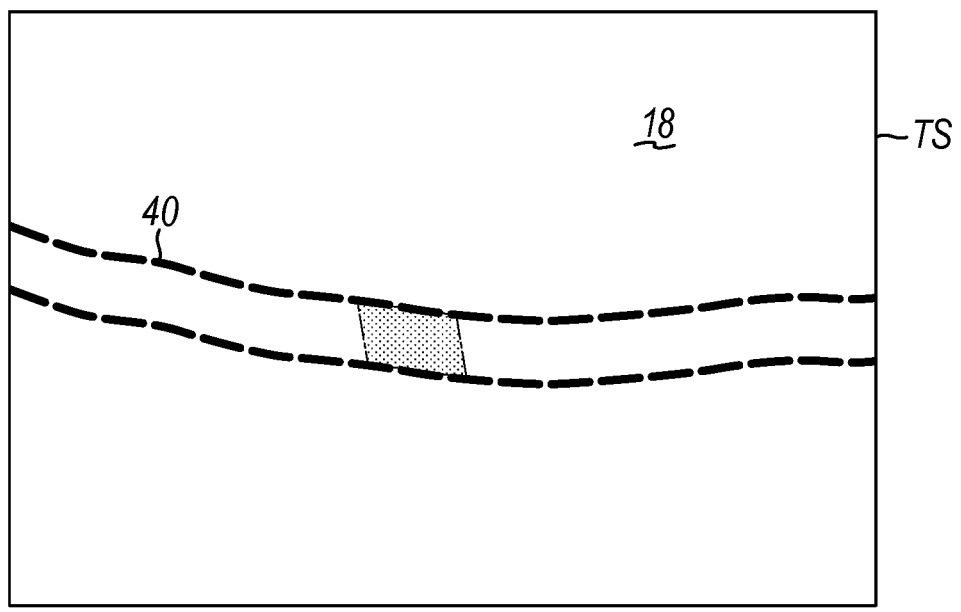
FIG. 7B depicts an enlarged schematic view of the treatment site of FIG. 6, showing a portion of the posterior nasal nerve after having been ablated by the application of RF energy as shown in FIG. 7A.

As shown in FIG. 7A, endoscope (120) is suitably manipulated to position ablation head (150) against the portion of nasal wall (18) that overlies the target posterior nasal nerve (40) at the treatment site (TS). Ablation head electrodes (154, 156) are then activated to deliver bipolar RF energy to nerve (40), through nasal wall (18), to thereby ablate the nerve (40). When full ablation of the nerve (40) is achieved, which may be determined via one or tissue sensors as described above, ablation head (150) is removed from contact with nasal wall (18) and instrument assembly (110) is retracted from the nasal cavity (10), leaving the posterior nasal nerve (40) in the ablated state shown in FIG. 7B. Advantageously, such a neurectomy of the posterior nasal nerve (40) via RF ablation is effective to treat intractable cases of rhinitis in a patient without damaging the patient's lacrimal gland and causing associated adverse health conditions, such as dry eye.

Following the surgical procedure, RF ablation instrument (140) may be separated from endoscope shaft (124) and disposed of; and replaced with a fresh RF ablation instrument (140) for a subsequent surgical procedure. In other examples, RF ablation instrument (140) may be configured to undergo sterilization along with endoscope (120), such that RF ablation instrument (140) may be reused multiple times.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an elongate shaft having a proximal shaft portion and a malleable distal shaft portion, wherein the elongate shaft is configured to be secured to a supporting surgical instrument; and (b) an ablation head coupled to the malleable distal shaft portion, wherein the ablation head includes at least one electrode operable to deliver RF energy to tissue for ablating the tissue, wherein the ablation head is sized to fit within the nasal cavity of a patient with a distal end of the supporting surgical instrument, wherein the proximal shaft portion is configured to operatively couple with an RF energy source operable to energize the at least one electrode with RF energy, wherein the malleable distal shaft portion is configured to bend relative to a longitudinal shaft axis defined by the proximal shaft portion for selectively orienting the ablation head relative to the longitudinal shaft axis.

Example 2

The surgical instrument of Example 1, wherein the at least one electrode comprises first and second electrodes operable to deliver bipolar RF energy to tissue.

Example 3

The surgical instrument of any of the preceding Examples, wherein the ablation head defines a distal end of the RF ablation instrument.

Example 4

The surgical instrument of any of the preceding Examples, wherein the ablation head extends distally from the malleable distal shaft portion along a head axis, wherein the malleable distal shaft portion is configured to bend relative to the longitudinal shaft axis to orient the ablation head in a position in which the head axis is offset from and parallel to the longitudinal shaft axis.

Example 5

The surgical instrument of any of the preceding Examples, wherein the ablation head comprises a planar surface, wherein the at least one electrode is disposed on the planar surface.

Example 6

The surgical instrument of any of the preceding Examples, wherein the ablation head is rectangular.

Example 7

The surgical instrument of any of the preceding Examples, further comprising an electrical conductor housed within the elongate shaft, wherein the electrical conductor is configured to electrically couple the at least one electrode of the ablation head with the RF energy source.

Example 8

The surgical instrument of any of the preceding Examples, wherein the elongate shaft comprises an electrically conductive material configured to electrically couple the at least one electrode of the ablation head with the RF energy source.

Example 9

The surgical instrument of any of the preceding Examples, further comprising an electrical connector coupled with the proximal shaft portion, wherein the electrical connector is configured to releasably couple with the RF energy source to place the at least one electrode in electric communication with the RF energy source.

Example 10

A surgical instrument assembly comprising: (a) an endoscope, wherein the endoscope comprises: (i) an endoscope shaft, and (ii) a distal end through which the endoscope is configured to capture an image of patient anatomy; and (b) the surgical instrument of any of the preceding Examples, wherein the proximal shaft portion of the surgical instrument is secured relative to the endoscope shaft.

Example 11

The surgical instrument assembly of Example 10, wherein the ablation head is configured to be positioned within a field of view of the distal end of the endoscope.

Example 12

The surgical instrument assembly of any of Examples 10 through 11, wherein the proximal shaft portion of the surgical instrument extends parallel to the endoscope shaft.

Example 13

The surgical instrument assembly of any of Examples 10 through 12, wherein the proximal shaft portion of the surgical instrument is in contact with the endoscope shaft, wherein the ablation head is configured to assume a position in which the ablation head is spaced apart from the endoscope shaft.

Example 14

The surgical instrument assembly of any of Examples 10 through 13, wherein the ablation head includes a first surface that faces toward the endoscope shaft and an opposed second surface that faces away from the endoscope shaft, wherein the at least one electrode is disposed on the second surface.

Example 15

The surgical instrument assembly of any of Examples 10 through 14, wherein the endoscope further comprises a handle from which the endoscope shaft extends distally, wherein the endoscope shaft and the surgical instrument are rotatable together relative to the handle about a longitudinal axis defined by the endoscope shaft.

Example 16

A surgical instrument assembly comprising: (a) an endoscope, wherein the endoscope includes an elongate shaft having a distal shaft end through which the endoscope is configured to capture an image of patient anatomy; and (b) an RF ablation instrument secured relative to the elongate shaft of the endoscope, wherein the RF ablation instrument comprises: (i) a malleable shaft portion, and (ii) an ablation head secured to a distal end of the malleable shaft portion, wherein the ablation head includes at least one electrode operable to ablate patient tissue with RF energy, wherein the ablation head is sized to fit within the nasal cavity of a patient, wherein the malleable shaft portion is configured to bend for selectively orienting the ablation head relative to the distal shaft end of the endoscope.

Example 17

The surgical instrument assembly of Example 16, wherein the at least one electrode comprises first and second electrodes operable to deliver bipolar RF energy to tissue.

Example 18

The surgical instrument assembly of any of Examples 16 through 17, wherein a proximal end of the RF ablation instrument includes an electrical connector configured to releasably couple with an RF energy source operable to deliver RF energy to the at least one electrode.

Example 19

A method of ablating a posterior nasal nerve of a patient with a surgical instrument assembly comprising an endoscope and an RF ablation instrument, wherein the endoscope includes a distal end configured to capture an image of patient anatomy, wherein the RF ablation instrument is secured to the endoscope and includes a malleable shaft portion and an ablation head having an electrode, the method comprising: (a) bending the malleable shaft portion of the RF ablation instrument to position the ablation head within a field of view of the distal end of the endoscope; (b) inserting the distal end of the endoscope and the ablation head into a nasal cavity of a patient; (c) under visualization provided by the endoscope, positioning the electrode of the ablation head in electrical contact with tissue overlying a posterior nasal nerve of the patient; and (d) energizing the electrode with RF energy to thereby ablate a portion of the posterior nasal nerve with the RF energy.

Example 20

The method of Example 19, wherein the ablation head includes first and second electrodes, wherein ablating the posterior nasal nerve with RF energy comprises positioning the first and second electrodes in electrical contact with the tissue overlying the posterior nasal nerve and delivering bipolar RF energy to the tissue.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument assembly comprising:
   (a) an endoscope, the endoscope including an elongate shaft defining a longitudinal axis and having a distal end, the endoscope having a window with a field of view oriented transversely relative to the longitudinal axis such that the field of view includes a region proximal to the distal end; and
   (b) a surgical instrument comprising:
      (i) an elongate shaft having a proximal shaft portion and a malleable distal shaft portion, a proximal end of the malleable distal shaft portion being fixedly secured to a distal end of the proximal shaft portion, the elongate shaft being secured to the endoscope such that the proximal shaft portion is fixed against longitudinal movement relative to the endoscope; and
      (ii) an ablation head coupled to the malleable distal shaft portion, the ablation head including at least one electrode operable to deliver RF energy to tissue for ablating the tissue, the ablation head being sized to fit within a nasal cavity of a patient with the distal end of the endoscope, at least a portion of the ablation head being configured to be within the field of view,
      the proximal shaft portion being configured to operatively couple with an RF energy source operable to energize the at least one electrode with RF energy,
      the malleable distal shaft portion being configured to bend relative to a longitudinal shaft axis defined by the proximal shaft portion for selectively orienting the ablation head relative to the longitudinal shaft axis.

2. The surgical instrument of claim 1, the at least one electrode comprising first and second electrodes operable to deliver bipolar RF energy to tissue.

3. The surgical instrument of claim 1, the ablation head defining a distal end of an RF ablation instrument.

4. The surgical instrument of claim 1, the ablation head extending distally from the malleable distal shaft portion along a head axis, the malleable distal shaft portion being configured to bend relative to the longitudinal shaft axis to orient the ablation head in a position in which the head axis is offset from and parallel to the longitudinal shaft axis.

5. The surgical instrument of claim 1, the ablation head comprising a planar surface, the at least one electrode being disposed on the planar surface.

6. The surgical instrument of claim 1, the ablation head being rectangular.

7. The surgical instrument of claim 1, further comprising an electrical conductor housed within the elongate shaft, the electrical conductor being configured to electrically couple the at least one electrode of the ablation head with the RF energy source.

8. The surgical instrument of claim 1, the elongate shaft comprising an electrically conductive material configured to electrically couple the at least one electrode of the ablation head with the RF energy source.

9. The surgical instrument of claim 1, further comprising an electrical connector coupled with the proximal shaft portion, the electrical connector being configured to releasably couple with the RF energy source to place the at least one electrode in electric communication with the RF energy source.

10. The surgical instrument assembly of claim 1, the ablation head being configured to be positioned within a field of view of the distal end of the endoscope.

11. The surgical instrument assembly of claim 1, the proximal shaft portion of the surgical instrument extending parallel to the elongate shaft of the endoscope.

12. The surgical instrument assembly of claim 1, the proximal shaft portion of the surgical instrument being in contact with the elongate shaft of the endoscope, the ablation head being configured to assume a position in which the ablation head is spaced apart from the elongate shaft of the endoscope.

13. The surgical instrument assembly of claim 1, the ablation head including a first surface that faces toward the elongate shaft of the endoscope and an opposed second surface that faces away from the elongate shaft of the endoscope, the at least one electrode being disposed on the second surface.

14. The surgical instrument assembly of claim 1, the endoscope further comprising a handle from which the elongate shaft of the endoscope extends distally, the elongate shaft of the endoscope and the surgical instrument being rotatable together relative to the handle about a longitudinal axis defined by the elongate shaft of the endoscope.

15. A surgical instrument assembly comprising:
(a) an endoscope, the endoscope including an elongate shaft having a longitudinal axis and a distal shaft end through which the endoscope is configured with a field of view, the field of view being oriented transversely relative to the longitudinal axis and encompassing a region proximal to the distal shaft end; and
(b) an RF ablation instrument fixedly secured relative to the elongate shaft of the endoscope, the RF ablation instrument comprising:
(i) a malleable shaft portion, and
(ii) an ablation head secured to a distal end of the malleable shaft portion, the ablation head including at least one electrode operable to ablate patient tissue with RF energy, the ablation head being sized to fit within a nasal cavity of a patient,
the malleable shaft portion being configured to bend for selectively positioning the ablation head within the field of view.

16. The surgical instrument assembly of claim 15, the at least one electrode comprising first and second electrodes operable to deliver bipolar RF energy to tissue.

17. The surgical instrument assembly of claim 15, a proximal end of the RF ablation instrument including an electrical connector configured to releasably couple with an RF energy source operable to deliver RF energy to the at least one electrode.

18. A method of ablating a posterior nasal nerve of a patient with a surgical instrument assembly comprising an endoscope and an RF ablation instrument, the endoscope defining a longitudinal axis and includes a distal end configured to capture an image of patient anatomy within a field of view that includes a region that is lateral to the longitudinal axis and proximal to the distal end, the RF ablation instrument being—fixedly—secured to the endoscope and including a malleable shaft portion and an ablation head having an electrode, the method comprising:
(a) bending the malleable shaft portion of the RF ablation instrument to position the ablation head within the field of view;
(b) inserting the distal end of the endoscope and the ablation head into a nasal cavity of a patient while the ablation head is exposed to the nasal cavity of the patient;
(c) under visualization provided by the endoscope via the field of view, positioning the electrode of the ablation head laterally relative to the longitudinal axis, with at least a portion of the ablation head being positioned proximally in relation to the distal end while still being within the field of view, and in electrical contact with tissue overlying a posterior nasal nerve of the patient; and
(d) energizing the electrode with RF energy to thereby ablate a portion of the posterior nasal nerve with the RF energy.

19. The method of claim 18, the ablation head including first and second electrodes, ablating the posterior nasal nerve with RF energy comprising positioning the first and second electrodes in electrical contact with the tissue overlying the posterior nasal nerve and delivering bipolar RF energy to the tissue.

20. The method of claim 18, bending the malleable shaft portion comprising bending the malleable shaft portion to position the ablation head at a first location relative to the distal end of the endoscope, inserting the distal end of the endoscope and positioning the electrode of the ablation head each being performed while maintaining the ablation head at the first location relative to the distal end of the endoscope.

* * * * *